United States Patent [19]

Yamato et al.

[11] 4,283,343

[45] Aug. 11, 1981

[54] PROCESS FOR PRODUCING LIQUID DIBASIC ACID ANHYDRIDES

[75] Inventors: Motoyuki Yamato, Kamakura; Tadao Natsuume, Yokosuka, both of Japan

[73] Assignee: Nippon Zeon Co. Ltd., Tokyo, Japan

[21] Appl. No.: 105,247

[22] Filed: Dec. 19, 1979

[30] Foreign Application Priority Data

Dec. 28, 1978 [JP] Japan .................................. 53-164297

[51] Int. Cl.$^3$ ........................................... C07D 307/89
[52] U.S. Cl. ................................................... 260/346.3
[58] Field of Search ...................................... 260/346.3

[56] References Cited

U.S. PATENT DOCUMENTS

| | | | |
|---|---|---|---|
| 2,764,597 | 9/1956 | Barney | 260/346.3 |
| 2,959,599 | 11/1960 | Bailey | 260/346.3 |
| 3,470,132 | 9/1969 | Ernst et al. | 260/47 |
| 3,470,214 | 9/1969 | Young | 260/346.3 |
| 3,647,701 | 3/1972 | Robinson et al. | 252/182 |

FOREIGN PATENT DOCUMENTS 54-48739 4/1979 Japan .

OTHER PUBLICATIONS

Beilstein, Third & Fourth Compilation, vol. 17 (1975), pp. 6001–6003.

*Primary Examiner*—Henry R. Jiles
*Assistant Examiner*—Bernard Dentz
*Attorney, Agent, or Firm*—Sherman & Shalloway

[57] ABSTRACT

A dibasic acid anhydride which is liquid at 0° C., or even at −20° C., is produced by heat-treating in the presence of a stereoisomerization catalyst a structural isomeric mixture obtained by shifting the double bond of methyl-tetrahydrophthalic anhydride. The liquid dibasic acid anhydride is useful as a curing agent for epoxy resins.

9 Claims, No Drawings

PROCESS FOR PRODUCING LIQUID DIBASIC ACID ANHYDRIDES

This invention relates to a process for producing a dibasic acid anhydride which is liquid at 0° C. More specifically, this invention relates to a process for producing a liquid dibasic acid anhydride suitable as a curing agent for epoxy resins, which comprises heat-treating a structural isomeric mixture of methyl-tetrahydrophthalic anhydride in the presence of a stereoisomerization catalyst.

Methyl-tetrahydrophthalic anhydride (to be referred to as Me-THPA) has been widely used as a curing agent for epoxy resins or as a component of unsaturated polyester resins. A structural isomeric mixture of Me-THPA which is obtained by shifting the double bond of its cyclohexene ring has properties suitable for use as a curing agent for epoxy resins, as disclosed, for example, in U.S. Pat. Nos. 3,470,214 and 3,470,132. For example, since it is liquid at room temperature, it lends itself to easy handling. It has superior storage stability because of its low sensitivity to moisture in the air. It also has a long pot life.

Maleic anhydride may remain in Me-THPA since it is a derivative of maleic anhydride. Thus, when an amine-type curing promoter generally used in compounding epoxy resins is added to such Me-THPA, a bubbling phenomenon attributed to the evolution of carbon dioxide gas, etc. occurs. This leads to the defect that during storage or transportation, drum containers are broken, cured articles of epoxy resins are colored, or the electrical properties of the cured articles are deteriorated.

It is the general practice therefore to remove the unreacted maleic anhydride by increasing the mole ratio of a conjugated diene to maleic anhydride, or prolonging the reaction time, or treating the addition reaction product further with a highly active conjugated diene, in the synthesis of Me-THPA. Even when the content of remaining maleic anhydride is reduced by these techniques, the bubbling phenomenon cannot be completely inhibited, and during storage in the summertime or at high temperatures, carbon dioxide gas, etc. are still generated.

It is an object of this invention therefore to remedy this defect of a structural isomeric mixture of Me-THPA, and to provide a liquid dibasic anhydride which yields practically no carbon dioxide gas when an amine-type curing promoter is added thereto.

This object can be achieved by heat-treating in the presence of a stereoisomerization catalyst a structural isomeric mixture of Me-THPA obtained by shifting its double bond.

In the present invention, the structural isomeric mixture of Me-THPA is first synthesized. 3-Me-$\Delta^4$-THPA, 4-Me-$\Delta^4$-THPA, and 1-Me-$\Delta^4$-THPA are specific examples of the Me-THPA used. The structural isomeric mixture can be obtained be heat-treating them either singly or as a mixture in the presence of a structural isomerization catalyst. 3-Me-$\Delta^4$-THPA and 4-Me-$\Delta^4$-THPA are preferred because they are readily available. The use of a mixture of 80 to 30% by weight of 3-Me-$\Delta^4$-THPA and 20 to 70% by weight of 4-Me-$\Delta^4$-THPA has the advantage that a low-melting product can be easily obtained under milder isomerization conditions than in the case of using them singly. It is not essential to synthesize the structural isomeric mixture in situ. Alternatively, it can be prepared by mixing at least two isomers (for example, 3-Me-$\Delta^4$-THPA and 3-Me-$\Delta^3$-THPA) separately produced.

It has previously been known to structurally isomerize Me-THPA to obtain an isomeric mixture. Known techniques include a method which comprises treating Me-THPA at 70° to 230° C. using an inorganic acid such as sulfuric acid or phosphoric acid as a catalyst (U.S. Pat. No. 2,959,599), a method which comprises treating Me-THPA at 100° to 250° C. using silica-alumina or an acidic ion exchange resin as a catalyst (U.S. Pat. No. 3,470,214), and a method which comprises treating Me-THPA at 120° to 175° C. as an organic sulfonic acid such as p-toluenesulfonic acid or dodecylbenzenesulfonic acid (U.S. Pat. No. 3,647,701). The present invention is not limited to these known methods, and any method which can induce structural isomerization can be used. A method which involves simultaneous performance of structural isomerization and disproportionation using a palladium or ruthenium catalyst is also known (U.S. Pat. No. 2,764,597). This method can also be used in this invention.

The melting point of the structural isomeric mixture used in this invention is not particularly limited so long as a product which is liquid at 0° C. is finally obtained. Usually, however, the melting point of the structural isomeric mixture is not more than 35° C., preferably not more than 20° C. To obtain a low-melting product, it is advantageous to use a structural isomeric mixture having a melting point of not more than 0° C.

According to the process of this invention, the resulting structural isomeric mixture of Me-THPA is heat-treated in the presence of a stereoisomerization catalyst. Examples of the stereoisomerization catalyst include tertiary amines (see Japanese Patent Application No. 59423/78) such as trimethylamine, triethylamine, dibutylaniline, pyridine, triethanolamine and 2,4,6-tris(dimethylaminomethyl) phenol; quaternary ammonium compounds (see U.S. Patent Application Ser. No. 034,504) such as ammonium chloride, ammonium sulfate, ammonium hydroxide, monoethylamine hydrochloride, aniline hydrochloride, tetramethyl ammonium chloride and tetramethyl ammonium hydroxide; nitrogen-containing compounds having a nitrogen atom at the carbon atom of the carbonyl group (see U.S. Patent Application Ser. No. 034,502) such as N,N-dimethylformamide, phthalimide, tetramethylurea and N-methylbiuret; basic metal oxides (see Japanese Patent Application No. 68355/78) such as calcium oxide, magnesium oxide and barium oxide; phosphorus compounds (see Japanese Patent Application No. 73982/78) such as triethyl phosphine, triphenyl phosphine, triethyl phosphite, triethyl phosphite and triethyl trithiophosphite; and alkali metal compounds (see Japanese Laid-Open Patent Publication No. 48739/79) such a lithium hydroxide and sodium hydroxide.

Any other materials which function as a catalyst in stereoisomerization can be used in this invention.

The heat-treating conditions for stereoisomerization differ depending upon the type and amount of the catalyst used, the melting point of the desired product, etc. Usually, the heat-treatment is carried out in an inert gaseous atmosphere such as nitrogen or argon at 60° to 300° C., preferably 80° to 250° C., for 1 second to 30 hours, preferably 5 minutes to 10 hours, using the catalyst in an amount of 0.001 to 20 parts by weight, preferably 0.005 to 15 parts by weight, per 100 parts by weight of the structural isomeric mixture of Me-THPA. As the heat-treating conditions become milder, the effect of inhibiting gas evolution decreases. Conversely, when the heat-treating conditions become severe, decomposition or coloration of Me-THPA tends to occur. The heat-treatment may be performed as an independent step, but it is effective to perform it such that it concurrently induces distillation for the removal of impurities.

The stereoisomerization by this heat-treatment gives a product which has a lower melting point, and is liquid even at a temperature of as low as $-20°$ C., and which shows practically no bubbling phenomenon when mixed with an amine-type curing promoter.

In addition to the aforesaid properties, the resulting dibasic acid anhydride has the advantages which the structural isomeric mixture of Me-THPA has, namely good storage stability and a long pot life. Accordingly, it is very useful as a curing agent for epoxy resins.

The following Examples further illustrate the present invention. All parts in these examples are by weight.

EXAMPLE 1

A 500 ml separable flask equipped with a stirrer was charged with 100 parts of 4-Me-$\Delta^4$-THPA having a melting point of 64° C. and 1 part of dodecylbenzenesulfonic acid, and the reaction was performed at 160° C. for 5 hours in an atmosphere of nitrogen. Distillation of the reaction mixture afforded a liquid structural isomeric mixture. Gas-chromatographic analysis of the isomeric mixture showed that the content of unreacted maleic anhydride was 250 ppm.

Triethylamine (0.1 part) was added to 100 parts of the structural isomeric mixture. The mixture was heat-treated at 200° C. for 3 hours in an atmosphere of nitrogen, and distilled to afford a liquid product.

The melting points of the structural isomeric mixture and the resulting product were measured. The state of bubbling upon the addition of a tertiary amine and the state of coloration upon mixture with an ordinary epoxy resin were evaluated by the following techniques. The results are shown in Table 1.

(1) State of bubbling

One hundred parts of 4-Me-THPA was uniformly mixed with 1 part of 2,4,6-tris-(dimethylaminomethyl)-phenol. The mixture was placed in a 1-liter oil drum, and stored at 50° C. for 1 month. The state of bulging of the drum was observed. It was rated as o when no bulging was observed, and as x when bulging was observed.

(2) State of coloration

One hundred parts of an epoxy resin (Epikote 828, a trademark for a product of Shell Chemical Co.), 79 parts of 4-Me-THPA and 1 part of 2,4,6-tris-(dimethylaminomethyl)phenol were mixed, and allowed to stand at 80° C. for 5 hours. The state of coloration was observed.

TABLE 1

|  | Melting point (°C.) | State of bubbling | State of coloration |
|---|---|---|---|
| Structural isomeric mixture | $-20>$ | x | Brown |
| Product | $-20>$ | o | Pale brown |

The results shown in Table 1 demonstrate that by heat-treating the structural isomeric mixture in the presence of triethylamine, the defects of the structural isomeric mixture are remedied.

EXAMPLE 2

One hundred parts of Me-THPA of the composition shown in Table 2 was mixed with 5 parts of an acidic ion exchange resin (Amberlyst 15, a trademark for a product of Rohm & Haas Company), and heated at 80° C. for 2 hours in a nitrogen atmosphere. The ion exchange resin was removed by a glass filter. Triethylamine (0.1 part) was added to 100 parts of the resulting structural isomeric mixture, and the mixture was heat-treated at 200° C. for 3 hours, and distilled under reduced pressure to afford a product. The properties of the isomeric mixture and the product were examined in the same way as in Example 1. The results are shown in Table 2.

TABLE 2

|  | Invention | | | | Control |
|---|---|---|---|---|---|
| Run No. | 1 | 2 | 3 | 4 | 5 |
| Compounding | | | | | |
| 3-Me-THPA (mp. 61° C.) | 100 | 75 | 50 | 25 | 0 |
| 4-Me-THPA (mp. 64° C.) | 0 | 25 | 50 | 75 | 100 |
| Structural isomeric mixture | | | | | |
| Melting point (°C.) | 53 | 32 | $-20>$ | 20 | 41 |
| State of bubbling | Un-measurable | x | x | x | x |
| Product | | | | | |
| Melting point (°C.) | 0 | $-20>$ | $-20>$ | $-5$ | 35 |
| State of bubbling | o | o | o | o | o |

It is seen from these results that when a mixture of 3-Me-THPA and 4-Me-THPA is used, a low-melting product can be easily obtained even under mild treating conditions.

EXAMPLE 3

Run No. 3 of Example 2 was repeated except that each of the compounds shown in Table 3 was used in the indicated amounts instead of the triethylamine used in Example 2. The results are shown in Table 3.

TABLE 3

|  | Invention | | | | |
|---|---|---|---|---|---|
| Run No. | 1 | 2 | 3 | 4 | 5 |
| Compound | Tetraethyl ammonium chloride | Dimethyl formamide | Calcium oxide | Triethyl phosphine | Lithium hydroxide |
| Amount (parts) | 0.1 | 0.1 | 10 | 0.8 | 0.01 |
| Melting point | $-20>$ | $-20>$ | $-20>$ | $-20>$ | $-20>$ |
| State of bubbling | o | o | o | o | o |

It is seen from these results that similar effects can be obtained even when compounds other than tertiary amines are used as a stereoisomerization catalyst.

What we claim is:
1. A process for producing a dibasic acid anhydride which is liquid at 0° C., comprising heat-treating in the presence of a stereoisomerization catalyst a structural isomeric mixture of methyltetrahydrophthalic anhydride resulting from the shifting of its double bond.

2. The process of claim 1 wherein said dibasic acid anhydride has a melting point of not more than −20° C.

3. The process of claim 1 wherein said methyltetrahydrophthalic anhydride is 3-methyl-tetrahydrophthalic anhydride, 4-methyl-tetrahydrophthalic anhydride, or a mixture of these.

4. The process of claim 1 wherein said methyl-tetrahydrophthalic anhydride is a mixture of 80 to 30% by weight of 3-methyl-tetrahydrophthalic anhydride and 20 to 70% by weight of 4-methyltetrahydrophthalic anhydride.

5. The process of claim 1 wherein said structural isomeric mixture has a melting point of not more than 35° C.

6. The process of claim 1 wherein said heat-treatment is carried out at a temperature of 60° to 300° C.

7. The process of claim 1 wherein the stereoisomerization catalyst is selected from the group consisting of trimethylamine, triethylamine, dibutylaniline, pyridine, triethanolamine, 2,4,6-tris (dimethylaminomethyl)-phenol; ammonium chloride, ammonium sulfate, ammonium hydroxide, monoethylamine hydrochloride, tetramethyl ammonium hydroxide, N, N-dimethylformamide, phthalimide, tetramethylurea, N-methylbiuret; calcium oxide, magnesium oxide, barium oxide, triethyl phosphine, triphenyl phosphine, triethyl phosphite, triethyl trithiophosphite, lithium hydroxide and sodium hydroxide.

8. The process of claim 1 wherein the heat treatment is conducted in an inert gaseous atmosphere at a temperature of 60° to 300° C. for a period from 1 second to 30 hours, the catalyst being used in an amount of 0.001 to 20 parts by weight per 100 parts by weight of the isomeric mixture of methyltetrahydrophthalic anhydride.

9. The process of claim 8 wherein the heat treatment is conducted at a temperature of 80° to 250° C. for a period of 5 minutes to 10 hours, the catalyst being used in an amount of 0.005 to 15 parts by weight per 100 parts by weight of the isomeric mixture of methyltetrahydrophthalic anhydride.

* * * * *

UNITED STATES PATENT AND TRADEMARK OFFICE
CERTIFICATE OF CORRECTION

PATENT NO. : 4,283,343

DATED : August 11, 1981

INVENTOR(S) : Yamato, et al.

It is certified that error appears in the above—identified patent and that said Letters Patent is hereby corrected as shown below:

Claim 7, lines 11-12 should read as follows:

"... and triethyl trithiophosphite [, lithium hydroxide and sodium hydroxide].

Signed and Sealed this

Twentieth Day of October 1981

[SEAL]

Attest:

Attesting Officer

GERALD J. MOSSINGHOFF

Commissioner of Patents and Trademarks